United States Patent
Mercer et al.

(10) Patent No.: US 7,326,725 B2
(45) Date of Patent: Feb. 5, 2008

(54) FUNGICIDAL COMPOSITION BASED ON AT LEAST ONE PYRIDYLMETHYLBENZAMIDE DERIVATIVES AND AT LEAST ON DITHIOCARBAMATE DERIVATIVE

(75) Inventors: Richard Mercer, Ecully (FR); Thomas Wegmann, Langenfeld (DE)

(73) Assignee: Bayer Cropscience S.A. (FR)

( * ) Notice: Subject to any disclaimer, the term of this patent is extended or adjusted under 35 U.S.C. 154(b) by 126 days.

(21) Appl. No.: 10/493,591

(22) PCT Filed: Oct. 21, 2002

(86) PCT No.: PCT/EP02/13789

§ 371 (c)(1),
(2), (4) Date: Apr. 23, 2004

(87) PCT Pub. No.: WO03/034824

PCT Pub. Date: May 1, 2003

(65) Prior Publication Data

US 2004/0266829 A1    Dec. 30, 2004

(30) Foreign Application Priority Data

Oct. 23, 2001   (FR) .................................. 01 13688

(51) Int. Cl.
*A01N 43/40* (2006.01)
*A01N 47/10* (2006.01)
*A01N 47/26* (2006.01)
*A01N 55/02* (2006.01)

(52) U.S. Cl. ...................... 514/357; 514/184; 514/185; 514/352; 514/491; 514/494; 514/500; 514/501; 514/502

(58) Field of Classification Search ................ 514/184, 514/185, 344–356, 491–492, 494, 499, 500, 514/501, 502, 357

See application file for complete search history.

(56) References Cited

U.S. PATENT DOCUMENTS 6,503,933 B1    1/2003   Moloney et al. ............. 514/357
6,828,441 B2   12/2004   Moloney et al. ............. 546/296

FOREIGN PATENT DOCUMENTS

| EP | 0398072 | 1/1990 |
| EP | 0472996 | 8/1991 |
| EP | 0775696 | 5/1995 |
| WO | WO 99 42447 | 8/1999 |
| WO | 03079788 | 10/2003 |

OTHER PUBLICATIONS

Farm Chemicals Handbook '98, Meister Publishing Co., Willoughby (Ohio), 1998, pp. C179, C241, C242, C260, C272, C324, C325 and C418.*

British Protection Council: "The Pesticide Manual, Twelfth Edition", CDS Tomlin (Ed), Farnham, GB XP002200421, n 343, p. 410-411; n 481, p. 578; n 482, p. 578-580; n 483, pp. 580-581; n 526, pp. 632-633; n 548, p.659; n 558, p. 669; n 652, pp. 781-782; n 809, pp. 962-963.

* cited by examiner

*Primary Examiner*—John Pak
(74) *Attorney, Agent, or Firm*—Ostrolenk, Faber, Gerb & Soffen, LLP

(57) ABSTRACT

1) Fungicidal compositions comprising: a) at least one pyridylmethylbenzamide derivative of formula (I), in which the various radicals are as defined in the description, and b) at least one compound (II) chosen from dithiocarbamates, preferably fungicidal dithiocarbamates, and, still more preferably from the following active agents: ferbam, mancopper, mancozeb, maneb, metiram, nabam, nickel bis(dimethyldithio-carbamate), propineb, zineb and mixtures thereof; and their agriculturally acceptable isomers and addition salts with an acid. 2) Method for the curative or preventive control of phytopathogenic fungi of crops using an effective and non-phytotoxic quantity of one of these fungicidal compositions.

17 Claims, No Drawings

FUNGICIDAL COMPOSITION BASED ON AT LEAST ONE PYRIDYLMETHYLBENZAMIDE DERIVATIVES AND AT LEAST ON DITHIOCARBAMATE DERIVATIVE

CROSS REFERENCE TO RELATED APPLICATION

The present application is a U.S. National Stage Application filed under 35 USC 371 of PCT/EP02/13789, filed on Oct. 21, 2002, which claims priority of French Application No. 01/13688, filed Oct. 23, 2001.

The present invention relates to combinations of fungicidal compounds intended in particular for protecting crops against fungal diseases, and the corresponding methods of protection by application of the said combinations.

More precisely, the subject of the present invention is novel fungicidal compositions based on pyridylmethylbenzamide and dithiocarbamate derivatives.

As regards fungicidal activity, in particular for the protection of crops, one of the problems at the heart of the research studies carried out in this technical field is the improvement of performances, in particular in terms of fungicidal activity and in particular in terms of maintaining this fungicidal activity over time.

Naturally, the fungicidal compounds useful for the protection of plants against fungi must be endowed with an ecotoxicity which is reduced to the minimum. As far as possible, they should not be dangerous or toxic to the operator during use.

Furthermore, it is advantageous for fungicidal compounds to have a broad activity spectrum.

The economic factor should of course not be overlooked in the search for novel fungicidal compounds.

Without being limiting, attention is paid more particularly in the context of the invention to protection against infestation, by fungi, of grapevine, cereals, fruits, vegetables, lucerne, soyabean, market garden crops, turf, wood and horticultural plants, among others.

The composition according to the invention include one or more compounds of the pyridylmethyl-benzamide type with fungicidal action as described in European patent application EP-A-1 056 723. These compounds make it possible to prevent the growth and development of phytopathogenic fungi (for example those which are active in the treatment of downy mildew, for example of grapevine, such as *Plasmopara viticola*).

This patent application EP-A-1 056 723 makes a general allusion to the possibility of combining these fungicidal active agents with products known to also develop a fungicidal activity, without citing by name examples of co-active ingredients, or even families of co-active ingredients, which are capable of being combined with pyridylmethylbenzamides.

One of the essential objectives of the present invention is to solve the problems set out above.

One of the essential objectives of the present invention is to provide novel fungicidal products which can be used, in particular by the farmer, for controlling the fungi infesting crops and in particular for controlling the major fungal diseases of grapevine such as downy mildew.

Another essential objective of the invention is to provide a novel fungicidal composition based on pyridylmethylbenzamide derivatives which is a lot more active against fungi which are harmful to plants, including grapevine, and which is in particular active over longer periods than the antifungal agents known up until now.

Another essential objective of the invention is to provide a novel fungicidal agent which is completely high-performing in particular as regards its efficacy against fungi and the perenniality of this efficacy so as to be able to reduce the doses of chemical products spread in the environment for combating fungal attacks of crops in particular vine downy mildew.

Another essential objective of the invention is to provide a novel fungicidal composition which is more active and active for longer, and which therefore has a lower dose, but which is also less toxic.

Another essential objective of the invention is to provide a novel broad-spectrum fungicidal composition which is perennially effective and which offers the farmer a large number of products so that the latter finds among them the product best suited to his particular use.

Another essential objective of the invention is to provide a novel fungicidal composition satisfying the specifications aimed at in the above objectives and which is also of a lower cost price, which is easy and which is not dangerous to handle.

Another essential objective of the invention is to provide a novel fungicidal composition as defined in the above objectives and which is useful in the preventive and curative treatment of fungal diseases, for example, of grapevine, cereals, Solanaceae, fruit, vegetables, lucerne, soyabean, market garden crops, turf, wood or horticultural plants.

Another essential objective of the invention is to provide a preventive and/or curative treatment of plants and in particular of crops, using a fungicidal composition or a fungicidal combination combining the products of the composition as defined in the above objectives, it being necessary for such a treatment to have a high and perennial efficacy against a very wide variety of fungi, while minimizing the doses, the toxicity and the cost.

Another essential objective of the present invention is to provide a kit for controlling, by way of curing and/or preventing and/or eradicating, the phytopathogenic fungi of plants and in particular of crops, such as grapevine, which meets the specifications set out in the objectives above.

An additional objective of the present invention is to allow improvement in the yield of the crops which is significant from an agronomic point of view.

All these objectives, among others, were achieved by the inventors who have had the merit of finding a fungicidal combination between pyridylmethylbenzamide derivatives and compounds of the dithiocarbamate type, preferably fungicides. Such a combination surprisingly and unexpectedly exhibiting a very high and perennial antifungal efficacy against a broad spectrum of fungi and in particular against those responsible for diseases such as vine downy mildew.

The present invention, which completely or partially satisfies the abovementioned objectives, therefore relates firstly to fungicidal compositions comprising:

a) at least one pyridylmethylbenzamide derivative of formula (I):

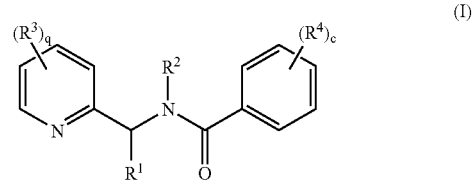

in which
- $R^1$ is chosen from a hydrogen atom, an optionally substituted alkyl radical and an optionally substituted acyl radical;
- $R^2$ is chosen from a hydrogen atom and an optionally substituted alkyl radical;
- $R^3$ and $R^4$, which are identical or different are independently chosen from a halogen atom, the hydroxyl radical, the cyano radical, the nitro radical, the radical —$SF_5$, the trialkylsilyl radical, an optionally substituted amino radical, an acyl radical, and a group E, OE or SE, in which E is chosen from an alkyl, alkenyl, alkynyl, cycloalkyl, cycloalkenyl, aryl and heterocyclyl radical, it being possible for each of them to be optionally substituted;
- c represents 0, 1, 2, 3 or 4;
- q represents 0, 1, 2, 3 or 4;

and their agriculturally acceptable possible optical and/or geometric isomers, tautomers and addition salts with an acid or a base;

and b) at least one compound (II) chosen from dithiocarbamates, and their agriculturally acceptable isomers and addition salts with an acid.

In the definitions of the compounds of formula (I) set out above, the various radicals and chemical terms used have, unless otherwise stated, the following meanings:

- "alkyl or alkyl-" denotes a linear or branched saturated hydrocarbon radical containing from 1 to 6 carbon atoms;
- "alkenyl" denotes a linear or branched hydrocarbon radical containing from 1 to 6 carbon atoms and an unsaturation in the form of double bond;
- "alkynyl" denotes a linear or branched hydrocarbon radical containing from 1 to 6 carbon atoms and an unsaturation in the form of a triple bond;
- "alkoxy" denotes an alkyloxy radical;
- "acyl" denotes the formyl radical or an alkoxycarbonyl radical;
- "cycloalkyl" denotes a saturated cyclic hydrocarbon radical containing from 3 to 8 carbon atoms;
- "aryl" denotes a phenyl or naphthyl radical:
- "heterocyclyl" denotes an unsaturated or a completely or partially saturated cyclic radical containing from 3 to 8 atoms, chosen from carbon, nitrogen, sulphur and oxygen, for example, and without limitation, pyridyl, pyridinyl, quinolyl, furyl, thienyl, pyrrolyl, oxazolinyl;
- the term "optionally substituted" means that the radicals thus termed may be substituted with one or more radicals chosen from chlorine, bromine, fluorine, iodine, alkyl, alkoxy, hydroxyl, nitro, amino; cyano and acyl.

The compounds of formula (I) are, for example, described in patent application EP-A-1 056 723 and, among these, the following will be preferred:

compounds possessing one of the following characteristics:
- $R^1$ and $R^2$, which are identical or different, are independently chosen from a hydrogen atom and an optionally substituted alkyl radical;
- $R^3$ and $R^4$, which are identical or different, are independently chosen from a halogen atom, the hydroxyl radical, the nitro radical, an optionally substituted amino radical, an acyl radical, and a group E, OE or SE, in which E is chosen from an alkyl, cycloalkyl, phenyl and heterocyclyl radical, it being possible for each of them to be optionally substituted;
- c represents 0, 1, 2 or 3;
- q represents 0, 1, 2 or 3;

and their agriculturally acceptable possible optical and/or geometric isomers, tautomers and addition salts with an acid or a base.

Among the compounds of formula (I), the following will also be preferred:

compounds possessing at least one of the following characteristics:
- $R^1$ and $R^2$, which are identical or different, are independently chosen from a hydrogen atom and a methyl or ethyl radical;
- $R^3$ and $R^4$, which are identical or different, are independently chosen from a halogen atom, the nitro radical, an optionally substituted amino radical and an alkyl, cycloalkyl, phenyl or heterocyclyl radical, it being possible for each of them to be optionally substituted;
- c represents 1 or 2;
- q represents 1 or 2;

and their agriculturally acceptable possible optical and/or geometric isomers, tautomers and addition salts with an acid or a base.

More particularly, the compounds of formula (I) are:
products possessing the following characteristics:
- $R^1$ and $R^2$ each represent a hydrogen atom;
- $R^3$ and $R^4$, which are identical or different, are independently chosen from a halogen atom, the nitro radical, an alkyl radical and the trifluoromethyl radical;
- c and q represent, independently of each other, 2;

and their agriculturally acceptable possible tautomers and addition salts with an acid or a base.

By way of examples, the following compounds of formula (I) are most particularly preferred in the context of the present invention:
- compound (Ia) which is 2,6-dichloro-N-{[3-chloro-5-(trifluoromethyl)-2-pyridinyl]methyl}-benzamide;
- compound (Ib) which is N-{[3-chloro-5-(trifluoromethyl)-2-pyridinyl]methyl}-2-fluoro-6-nitrobenzamide;
- compound (Ic) which is N-{[3-chloro-5-(trifluoromethyl)-2-pyridinyl]methyl}-2-methyl-6-nitrobenzamide, and their agriculturally acceptable possible tautomers and addition salts with an acid or a base.

The compounds (II) are preferably dithiocarbamates known for their fungicidal activity, and their agriculturally acceptable isomers and addition salts with an acid.

Still more preferably, the antifungal dithiocarbamate (II) is chosen from the group of compounds comprising: ferbam, mancopper, mancozeb, maneb, metiram, nabam, nickel bis (dimethyldithio-carbamate), propineb, zineb and mixtures thereof.

Advantageously, the compositions according to the present invention comprise:
compound (Ia) and/or compound (Ib) and/or compound (Ic) combined with mancozeb or propineb.

The preferred compositions of the present invention comprise compound (Ia) with mancozeb or propineb, and the possible tautomers and addition salts with an acid or a base of compound (Ia) and mancozeb or propineb, as long as these equivalents are agriculturally acceptable.

The fungicidal combination of compounds (I) with compounds (II) according to the invention, and in particular mancozeb or propineb, makes it possible to significantly improve the persistence of antifungal activity in the context of the curative and/or preventive treatment of major diseases of crops, including in particular those caused by fungi of the family of Peronosporaceae, in particular *Plasmopara viti-* cola (vine downy mildew), *Plasmopara halstedei* (sunflower mildew), *Pseudoperonospora* sp (in particular cucurbit mildew (*Pseudoperonospora cubensis*) and downy mildew of hops (*Pseudoperonospora humuli*)), *Bremia lactucae* (mildew of lettuce), *Peronospora tabacinae* (downy mildew of tobacco), *Peronospora destructor* (downy mildew of onion), *Peronospora parasitica* (downy mildew of cabbage), *Peronospora farinosa* (downy mildew of chicory and downy mildew of beetroot).

In particular, this combination has eradicant properties which are superior to those of the products alone.

From the point of view of weight, it should be specified that in accordance with the invention, the compound (I)/compound (II) ratio ranges most often from 1/500 to 30/1, preferably from 1/200 to 20/1, more preferably from 1/10 to 10/1.

The compound (I)/compound (II) ratio is defined as being the ratio by weight of these 2 compounds. The same applies to any ratio of 2 chemical compounds, which is subsequently measured in the present text, since a definition different from this ratio is not expressly given.

According to another aspect of the present invention, in the compositions according to the invention, the compound (I)/compound (II) ratio may be advantageously chosen so as to produce a synergistic effect. The term synergistic effect is understood to mean in particular that defined by Colby in an article entitled "Calculation of the synergistic and antagonistic responses of herbicide combinations" Weeds, (1967), 15, pages 20-22.

The latter article mentions the formula:

$$E = x + y - \frac{x * y}{100}$$

in which E represents the expected percentage of inhibition of the disease for the combination of the two fungicides at defined doses (for example equal to x and y respectively), x is the percentage of inhibition observed for the disease by the compound (I) at a defined dose (equal to x), y is the percentage of inhibition observed for the disease by the compound (II) at a defined dose (equal to y). When the percentage of inhibition observed for the combination is greater than E, there is a synergistic effect.

The term "synergistic effect" also means the effect defined by application of the Tammes method, "Isoboles, a graphic representation of synergism in pesticides", Netherlands Journal of Plant Pathology, 70(1964), pages 73-80.

The compound (I)/compound (II) ratio ranges indicated above do not in any way limit the scope of the invention, but are, rather, mentioned as a guide, a person skilled in the art being entirely capable of carrying out additional tests to find other values of the ratio of doses of these two compounds, in particular for which a synergistic effect is observed.

Advantageously, the compound (I)/compound (II) ratio is chosen so as to produce a synergistic effect.

Usually, the compositions according to the invention comprise between 0.00001 and 100%, preferably between 0.001 and 80%, of active compounds, whether these compounds are combined, or whether they are in the form of two active ingredients used separately.

It is clearly understood that the said fungicidal compositions may contain a single compound (I) or more than such a compound and/or a single compound (II) or more than such as compound, and one or more other fungicidal, herbicidal, insecticidal and/or plant growth regulating compounds, according to the use for which they are intended.

Thus, the fungicidal compositions according to the present invention may also comprise, for example, one or more other fungicidal active ingredients chosen from acibenzolar-S-methyl, azoxystrobin, benalaxyl, benomyl, blasticidin-S, bromuconazole, captafol, captan, carbendazim, carboxin, carpropamid, chlorothalonil, the fungicidal compositions based on copper and copper derivatives such as copper hydroxide and copper oxychloride, cyazofamid, cyflufenamid, cymoxanil, cyproconazole, cyprodinyl, dichloran, diclocymet, diethofencarb, difenoconazole, diflumetorim, dimethomorph, dimoxystrobin, diniconazole, discostrobin, dodemorph, dodine, edifenphos, epoxyconazole, ethaboxam, ethirimol, fenarimol, fenbuconazole, fenhexamid, fenoxanil, fenpiclonil, fenpropidin, fenpropimorph, ferimzone, fluazinam, fludioxonil, flumetover, fluquinconazole, flusilazole, flusulfamide, flutolanil, flutriafol, folpel, furalaxyl, furametpyr, guazatine, hexaconazole, hymexazol, imazalil, iprobenphos, iprodione, isoprothiolane, kasugamycin, kresoxim-methyl, mefenoxam, mepanipyrim, metalaxyl and its entantiomeric forms such as metalaxyl-M, metconazole, metiram-zinc, metominostrobin, metrafenone, nicobifen, oxadixyl, oxpoconazole, pefurazoate, penconazole, pencycuron, phosphorous acid and its derivatives such as fosetyl-Al, phthalide, picoxystrobin, probenazole, prochloraz, procymidone, propamocarb, propiconazole, pyraclostrobin, pyrimethanil, pyroquilon, quinoxyfen, silthiofam, simeconazole, spiroxamine, sup-l190, tebuconazole, tetraconazole, thiabendazole, thiflusamide, thiophanate, for example thiophanate-methyl, thiram, tiadinil, triadimefon, triadimenol, tricyclazole, tridemorph, trifloxystrobin, triticonazole, valinamide derivatives such as, for example, iprovalicarb, vinclozolin and zoxamide.

In addition to these additional active agents, the fungicidal compositions according to the invention may also contain any other excipient and/or auxiliary agent useful in plant protection formulations such as, for example, an agriculturally suitable inert carrier and optionally an agriculturally suitable surfactant.

As regards the presentations of the compositions according to the invention, it should be indicated that they are appropriate for a large number of formulations. Thus, it is possible to use these compositions as aerosol dispenser; bait (ready-to-use); concentrate for preparation of baits; stock bait; suspension of capsules; cold fogging concentrate; dustable powder; emulsifiable concentrate; aqueous/aqueous type emulsion; oil/inverse type emulsion; encapsulated granule; fine granule; suspension concentrate for seed treatment; compressed gas; gas generating product; grain bait; granular bait; granule; hot fogging concentrate; macrogranule; microgranule; oil-dispersible powder, oil miscible suspension concentrate; oil-miscible liquid; paste; plant rodlet; plate bait; powder for dry seed treatment; scrap bait; seeds coated with a pesticide; smoke candle; smoke cartridge; smoke generator; smoke pellet; smoke rodlet; smoke tablet; smoke tin; soluble concentrate; soluble powder; solution for seed treatment; suspension concentrate (=flowable concentrate); tracking powder; ultra low volume liquid; ultra low volume suspension; vapour releasing product; water-dispersible granules or tablets; water dispersible powder for slurry treatment; water-soluble granules or tablets; water-soluble powder for seed treatment; wettable powder.

These compositions cover not only the compositions which are ready to be applied to the crop to be treated by means of a suitable device, such as a spraying device, but also the commercial concentrated compositions which have to be diluted before application to the crop.

The compositions described below are used in general for application to growing plants, or to sites where crops are grown, or for the coating or film-coating of seeds.

The compositions according to the invention are, appropriately, applied to the vegetation and in particular to the leaves infested or capable of being infested with the phytopathogehic fungi. Another method of applying the compounds or compositions according to the invention is to add a formulation containing the active ingredients to the irrigation water. This irrigation may be an irrigation using sprinklers.

For their use in practice, the compositions according to the invention can be used alone and can also advantageously be used in formulations containing one or the other of the active ingredients or alternatively both of them together, in combination or association with one or more other compatible components which are, for example, solid or liquid fillers or diluents, adjuvants, surfactants or equivalents, which are suitable for the desired use and which are acceptable for uses in agriculture. The formulations can be of any type known in the sector which are suitable for application onto all types of plantations or crops. These formulations, which can be prepared in any manner known in this sector, also form part of the invention.

The formulations can also contain ingredients of other types, such as protective colloids, adhesives, thickeners, thixotropic agents, penetrating agents, oils for spraying, stabilizers, preserving agents (in particular mouldproofing agents), sequestering agents or the like, as well as other known active ingredients which have pesticidal properties (in particular fungicidal, insecticidal, acaricidal or nematocidal properties) or which have properties of regulating plant growth. More generally, the compounds used in the invention can be combined with any solid or liquid additives corresponding to the usual formulation techniques.

In the present account, the term "filler" means an organic or inorganic, natural or synthetic component with which the active components are combined to facilitate its application, for example, onto the plants, the seeds or the soil. This filler is consequently generally inert and it must be acceptable (for example acceptable for agronomic uses, in particular for treating plants).

The filler can be solid, for example clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates. The solid fillers which are suitable for granules are as follows: natural, crushed or broken rocks, such as calcite, marble, pumice, sepiolite and dolomite; synthetic granules of inorganic or organic flours; granules of organic material such as sawdust, coconut shell, corn ear or envelope, or tobacco stem; kieselguhr, tricalcium phosphate, powdered cork or adsorbent carbon black; water-soluble polymers, resins, waxes; or solid fertilizers. Such compositions can, if so desired, contain one or more compatible agents such as wetting agents, dispersing agents, emulsifiers or colourings which, when they are solid, can also act as diluents.

The fillers can also be liquid, for example: water, alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulphoxide, N,N-dimethylacetamide or N-methylpyrrolidone; N-octylpyrrolidone, liquefied gases; or the like, whether they are taken separately or as a mixture.

The surfactant can be an emulsifier, a dispersing agent or a wetting agent, of ionic or nonionic type or a mixture of these surfactants. Among those surfactants there are used, for example, polyacrylic acid salts, lignosulphonic acid salts, phenolsulphonic or naphthalenesulphonic acid salts, polycondensates of ethylene oxide with fatty alcohols or fatty acids or fatty esters or fatty amines, substituted phenols (in particular alkylphenols or arylphenols), ester-salts of sulphosuccinic acid, taurine derivatives (in particular alkyl taurates), phosphoric esters of alcohols or of polycondensates of ethylene oxide with phenols, fatty acid esters with polyols, or sulphate, sulphonate or phosphate functional derivatives of the compounds described above. The presence of at least one surfactant is generally essential when the active ingredients and/or the inert filler are insoluble or only sparingly soluble in water and when the filler for the said composition to be applied is water.

The formulations according to the invention can also contain other additives such as adhesives or colourings. Adhesives such as carboxymethylcellulose, or natural or synthetic polymers in the form of powders, granules or matrices, such as gum arabic, latex, polyvinylpyrrolidone, polyvinyl alcohol or polyvinyl acetate, natural phospholipids, such as cephalins or lecithins, or synthetic phospholipids can be used in the formulations. It is possible to use colourings such as inorganic pigments, such as, for example: iron oxides, titanium oxides, Prussian blue; organic colouringstuffs, such as those of the alizarin, azo or metal phthalocyanin type; or of trace elements such as iron, manganese, boron, copper, cobalt, molybdenum or zinc salts.

The formulations containing the compositions of the invention, which are used to control the phytopathogenic fungi of crops, can also contain stabilizers, other fungicidal agents, insecticides, acaricides, nematicides, anti-helminths or anti-coccidoses, bactericides, attractant or repellent agents, deodorizers, flavourings or colourings.

These can be chosen for the purpose of improving the strength, the persistence, the safety, and the spectrum of action on the phytopathogenic fungi of crops or to make the composition capable of accomplishing other useful functions for the areas treated.

For foliar applications, the choice of surfactants is crucial to ensure good bioavailability of the active ingredients; thus a combination of a surfactant with a hydrophilic character (HLB>10) and of a surfactant with a lipophilic character (HLB<5) will be preferably used. Such combinations of surfactants are, for example, described in French patent application No. 00 04015.

As regards the preparation of compounds (I), reference may be made to European patent application EP-A-1 056 723.

As regards the production of compounds (II), reference may be made to the book "The Electronic Pesticide Manual—Version 1.0"—British Crop Protection Council—Ed Clive Tomlin.

According to another of these objects, the invention relates to a method for controlling, by way of curing, preventing or eradicating, the phytopathogenic fungi of crops, characterized in that an effective (agronomically effective) and nonphytotoxic quantity of a fungicidal composition as defined above is applied to the soil where plants grow or are capable of growing, to the leaves and/or the fruits of plants or to the seeds of plants.

In this method, a composition is used which is prepared beforehand by mixing the 2 active compounds (I) and (II).

According to a variant of such a method of controlling, by way of curing, preventing or eradicating, the phytopathogenic fungi of crops:

a combination of at least one compound (I) and of at least one compound (II) as defined above is used;

the compounds (I) and (II) are applied simultaneously, separately or sequentially to the soil where plants grow or are capable of growing, to the leaves and/or the fruits of plants or to the seeds of plants, an effective (agronomically effective) and nonphytotoxic quantity.

This variant corresponds to a fresh preparation of the fungicidal composition.

It is also possible to apply simultaneously, successively or separately so as to have the conjugated (I)/(II) effect, of a composition each containing one of the two active ingredients (I) or (II).

Preferably, the fungicidal compositions according to the invention usually contain from 0.5 to 95% of the combination of compound (I) and compound (II). This may be the concentrated composition, that is to say the commercial product combining compound (I) and compound (II). This may also be the dilute composition ready to be applied to the crops to be treated. In the latter case, the dilution with water may be carried out either using a commercial concentrated composition containing compound (I) and compound (II) (this mixture is called ready mix), or using the tank mix of two commercial concentrated compositions each containing compound (I) and compound (II).

The treatment of crops against phytopathogenic diseases, using the fungicidal composition according to the invention, is carried out, for example, by application or by administration, with an effective and nonphytotoxic quantity of the abovementioned fungicidal composition or combination, to the aerial parts of the crops or to the soil where they grow, the said crops being those which are infested or which are capable of being infested by a phytopathogenic disease such as downy mildew, oidium, brown rust or *Septoria* disease. The expression treatment of the crop is also understood to mean the treatment of the reproductive products of the crop, such as the seeds or the tubers for example.

Under specific conditions, for example according to the nature of the phytopathogenic fungus to be treated, a lower dose may offer adequate protection. Conversely, certain climatic conditions, resistance or other factors may require higher doses of active ingredient.

The effective working doses of the combinations used in the invention can vary within wide proportions, in particular depending on the nature of the phytopathogenic fungi to be eliminated or the degree of infestation, for example, of the plants with these fungi.

The optimum dose usually depends on several factors, for example on the type of phytopathogenic fungus to be treated, on the type or level of development of the infested plant, on the density of vegetation, or alternatively on the method of application. More preferably, an effective dose of active ingredients (I) and (II) is between about 7 g/ha and about 10 000 g/ha.

Without it being limiting, the crop treated with the fungicidal composition or combination according to the invention is, for example, a cereal, but this could be grapevine, vegetables, fruits, lucerne, soyabean, market garden crops, turf, wood or horticultural plants.

The phytopathogenic fungi of crops which may be controlled by this method are selected from the group comprising:

the group of oomycetes:

of the family of Peronosporaceae, in particular *Plasmopara viticola* (vine downy mildew), *Plasmopara halstedei* (sunflower mildew), *Pseudoperonospora* sp (in particular cucurbit mildew (*Pseudoperonospora cubensis*) and downy mildew of hops (*Pseudoperonospora humuli*)), *Bremia lactucae* (mildew of lettuce), *Peronospora tabacinae* (downy mildew of tobacco), *Peronospora destructor* (downy mildew of onion), *Peronospora parasitica* (downy mildew of cabbage), *Peronospora farinosa* (downy mildew of chicory and downy mildew of beetroot);

of the genus *Phytophthora* such as *Phytophthora phaseoli*, *Phytophthora citrophthora*, *Phytophthora capsici*, *Phytophthora cactorum*, *Phytophthora palmivora*, *Phytophthora cinnamoni*, *Phytophthora megasperma*, *Phytophthora parasitica*, *Phytophthora fragariae*, *Phytophthora cryptogea*, *Phytophthora porri*, *Phytophthora nicotianae*, *Phytophthora infestans* (mildew of Solanaceae, in particular late blight of potato or tomato);

the group of adelomycetes (*ascomycetes*):

of the genus *Alternaria*, for example *Alternaria solani* (early blight of Solanaceae and in particular of tomato and potato), of the genus *Guignardia*, in particular *Guignardia bidwelli* (black rot of grapevine), of the genus *Venturia*, for example *Venturia inaequalis*, *Venturia pirina* (apple or pear scabs), of the genus *Oidium*, for example powdery mildew of grapevine (*Uncinula necator*); oidium of leguminous crops, for example *Erysiphe polygoni* (powdery mildew of Cruciferae); *Leveillula taurica*, *Erysiphe cichoracearum*, *Sphaerotheca fuligena* (powdery mildew of cucurbits, of composites and of tomato); *Erysiphe communis* (powdery mildew of beetroot and cabbage); *Erysiphe pisi* (powdery mildew of pea and lucerne); *Erysiphe polyphaga* (powdery mildew of haricot bean and cucumber); *Erysiphe umbelliferarum* (powdery mildew of ombellifera, in particular of carrot); *Sphaerotheca humuli* (hop mildew); powdery mildew of wheat and barley (*Erysiphe graminis* form a specie tritici and *Erysiphe graminis* form a specie hordei), of the genus *Taphrina*, for example *Taphrina deformans* (peach leaf curl), of the genus *Septoria*, for example *Septoria nodorum* or *Septoria tritici* (*Septoria* disease of cereals), of the genus *Sclerotinia*, for example *Sclerotinia sclerotinium*, of the genus *Pseudocercosporella*, for example *P. herpotrichoides* (eyespot of cereals), of the genus *Botrytis cinerea* (grapevine, vegetable and market garden crops, pea and the like), of the genus *Phomopsis viticola* (excoriosis of grapevine), of the genus *Pyrenospora*, of the genus *Helminthosporium*, for example *Helminthosporium tritici* repentis (yellow leaf spot of wheat) or *Helminthosporium teres* (yellow leaf spot of barley), of the genus *Drechslera* or *Pyrenophora*, of the group of *basidiomycetes* of the genus *Puccinia*, for example *Puccinia recondita* or *striiformis* (wheat rust), *Puccinia triticina*, *Puccinia hordei*, of the family *Rhizoctonia* spp, for example *Rhizoctonia solani*.

In addition to their fungicidal activities at the heart of the invention, the compositions or combinations defined above may also have a biocide action against bacteria and viruses, such as for example:

fire blight, *Erwinia amylovora;* bacterial streak of stone fruit trees, *Xanthomonas campestris;* pear blossom blight, *Pseudomonas syringae;* bacteriosis of rice and cereals;

the viruses present on rice, vegetable and cereal crops.

The crops envisaged in the context of the present invention are preferably grapevine, cereal crops (wheat, barley, maize, rice) and vegetable crops (haricot bean, onion, cucurbitaceae, cabbage, potato, tomato, sweet pepper, spinach, pea, lettuce, celery, chicory), fruit crops (strawberry plants, raspberry plants), tree crops (apple trees, pear trees, cherry trees, ginseng, lemon trees, coconut palms, pecan trees, cacao trees, walnut trees, rubber trees, olive trees, poplars, banana trees), sunflower, beetroot, tobacco, hop and ornamental crops.

A classification made, no longer based on the fungi or bacteria targeted, but on the target crops may be illustrated as below:

grapevine:, downy mildew (*Plasmopara viticola*), powdery mildew (*Uncinula necator*), grey mould (*Botrytis cinerea*), excoriosis (*Phomopsis viticola*) and black rot (*Guignardia bidwelli*), Solanaceae: blight (*Phytophthora infestans*), alternara disease (*Alternaria solani*) and grey mould (*Botrytis cinerea*), vegetable crops: downy mildew (*Peronospora* sp., *Bremia lactucae, Pseudoperonospora* sp), alternara (*Alternaria* sp.), sclerotinia disease (*Sclerotinia* sp.), grey mould (*Botrytis cinerea*), foot or root rot (*Rhizoctonia* spp.), powdery mildew (*Erysiphe* sp.; *Sphaerotheca fuliginea*), arboriculture: scab (*Venturia inaequalis, V. pirina*), bacterial diseases (*erwinia amylovora, xanthomonas campestris, pseudomonas syringae*), powdery mildew (*Podosphaera leucotricha*) and *Monilia* (*Monilia fructigena*), citrus: scab (*Elsinoe fawcetti*), melanose (*Phomopsis citri*) and *Phytophthora* sp. diseases, wheat, as regards controlling the following seed diseases: *Fusarium* diseases (*Microdochium nivale* and *Fusarium roseum*), smuts (*Tilletia caries, Tilletia controversa* or *Tilletia indica*), *Septoria* disease (*Septoria nodorum*), wheat, as regards controlling the following diseases of the aerial parts of the plant: eyespot (*Pseudocercosporella herpotrichoïdes*), take-all (*Gaeumannomyces graminis*), *Fusarium* disease of the foot (*F. culmorum, F. graminearum*), *Rhizoctonia* disease (*Rhizoctonia cerealis*), powdery mildew (*Erysiphe graminis* form a specie *tritici*), rusts (*Puccinia striiformis* and *Puccinia recondita*), *Septoria* diseases (*Septoria tritici* and *Septoria nodorum*) and yellow leaf spot of wheat (*Helminthosporium tritici-vulgaris*), wheat and barley, as regards controlling bacterial and viral diseases, for example barley yellow mosaic, barley, as regards controlling the following seed diseases: yellow leaf spot (*Pyrenophora graminea, Bipolaris, Pyrenophora teres* and *Cochliobolus sativus*), loose smut (*Ustilago nuda*) and *Fusarium* diseases (*Microdochium nivale* and *Fusarium roseum*), barley, as regards controlling the following diseases of the aerial parts of the plant: eyespot (*Pseudocercosporella herpotrichoïdes*), yellow leaf spot (*Pyrenophora teres* and *Cochliobolus sativus*), powdery mildew (*Erysiphe graminis* form a specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*) and certain virus diseases (virus Y);

cotton, as regards controlling the following diseases of young plants obtained from seeds: damping-off diseases and collar rot (*Rhizoctonia solani, Fusarium oxysporum*), black root rot (*Thielaviopsis basicola*), pea, as regards controlling the following seed diseases: anthracnose (*Ascochyta pisi, Mycosphaerella pinodes*), *Fusarium* disease (*Fusarium oxysporum*), grey mould (*Botrytis cinerea*), rust (*Uromyces pisi*), rape plant, as regards controlling the following seed diseases: *Phoma lingam* and *Alternaria brassicae*, grey mould (*Botrytis cinerea*), and sclerotinia disease (*Sclerotinia sclerotinium*), maize, as regards controlling seed diseases (*Rhizopus* sp., *Penicillium* sp., *Trichoderma* sp., *Aspergillus* sp. and *Gibberella fujikuroi*), yellow leaf spot (*Bipolaris*), *Fusarium* disease (*Fusarium oxysporum*), rice: foot and root rot (*Rhizoctonia* spp.), flax, as regards controlling seed disease (*Alternaria linicola*), banana: *Cercospora* disease (*Mycosphaerella figiensis*), turf: rust, powdery mildew, yellow leaf spot, terruric diseases (*Microdochium nivale, Pythium* sp., *Rhizoctonia solani, Sclerotinia homeocarpa*), forest trees, as regards controlling damping-off (*Fusarium oxysporum, Rhizoctonia solani*).

Very advantageously, the method for controlling plant diseases according to the invention has shown excellent results against grapevine diseases: downy mildew (*Plasmopara viticola*), powdery mildew (*Uncinula necator*), grey mould (*Botrytis cinerea*), excoriosis (*Phomopsis viticola*) and black rot (*Guignardia bidwelli*) and against vegetable crop diseases.

The expression "are applied to the plants to be treated" is understood to mean, for the purposes of the present text, that the fungicidal compositions which are the subject of the invention may be applied by means of various methods of treatment such as:

spraying onto the aerial parts of the said plants a liquid comprising one of the said compositions, dusting, the incorporation into the soil of granules or powders, spraying, around the said plants, and in the case of trees injection or daubing, coating or film-coating the seeds of the said plants with the aid of a plant-protection mixture comprising one of the said compositions.

Spraying a liquid onto the aerial parts of the crops to be treated is the preferred method of treatment.

The subject of the present invention is also a product comprising a compound (I) and a compound (II) as a combined preparation for simultaneous, separate or sequential use in controlling the phytopathogenic fungi of crops at a site.

Another object of the invention which is linked to the mode of preparing the composition according to the invention immediately before use consists of a kit for controlling, curatively or preventively, the phytopathogenic fungi of crops, characterized in that it comprises at least one compound (I) and at least one compound (II) as defined above, intended to be combined or used simultaneously, separately or sequentially in controlling the phytopathogenic fungi of crops at a site.

It is therefore a pack in which the user finds all the ingredients for preparing the fungicidal formulation which they wish to apply to the crops. These ingredients, which comprise in particular the active agents (I) and (II) and which are packaged separately, are provided, for example, in the form of a powder or in the form of a liquid which is concentrated to a greater or lesser degree. The user simply has to mix in the prescribed doses and to add the quantities of liquid, for example of water, necessary to obtain a formulation which is ready to use and which can be applied to the crops.

Most appropriate is a product for simultaneous, separate, alternate or sequential application of at least one fungicidal compound (I) and one fungicidal compound (II).

It goes without saying that the different variants which may be envisaged of the compositions and methods according to the invention form an integral part of the present invention; it being possible for the said different variants, moreover, to be combined or associated with each other without as a result departing either from the spirit or from the scope of the said invention.

In the same manner, the different aspects of the present invention which have just been described may be combined or associated with each other without as a result departing either from the spirit or from the scope of the said invention.

The following example is given purely by way of illustration of the invention and does not limit it in any manner.

EXAMPLE

It is intended to give an illustration of the efficacy of the compositions according to the invention on grapevine diseases, in particular the combinations combining compound (Ia), having the chemical name 2,6-dichloro-N-{[3-chloro-5-(trifluoromethyl)-2-pyridinyl]-methyl}benzamide, and compound (II) which is mancozeb in the form of a formulation 85 WP.

1-Conditions and objectives

The trials consisted in curative tests of 24 hours on grapevine infected with *Plasmopara viticola*.

2-Materials and methods

Protocol:

Grapevine (Chardonay variety) plants are grown on sandy soil in plastic pots, with one plant per pot. The plants which are two months old (6- to 7-leaf stage) are inoculated by spraying an aqueous suspension of *Plasmopara viticola* sporocysts obtained from infected leaves. The concentration of sporocysts is about 100 000 units per ml.

After infection, the inoculated plants are subjected to a curative treatment by spraying with compound (I) alone and compound (II) alone, and with a mixture of compound (I) and compound (II), in each case applied at a dose of 500 l/ha.

The studied compound (I)/compound (II) ratios are detailed in Table 1 below.

After infection and curative treatment, the plants are covered and left for six days at 20° C.

The infection is then assessed on a scale of 1 to 10, according to which 0 indicates that there is no infection and 10 that the infection level is 100%.

The percentage control of the disease (efficacy: see below) is calculated for each treatment with reference to the untreated plants and the expected results are calculated using the Colby formula (see below).

The difference between the real results and the expected results is used to determine the synergy between the two fungicidal compounds of the composition according to the invention.

The efficacy of the treatment is calculated using the following Abbott formula:

$$\text{Efficacy} = \frac{(\text{untreated}) - \text{treated}}{\text{untreated}} \times 100$$

Analysis of the results is carried out using the Colby model:

$$E = x + y - \frac{xy}{100}$$

in which E represents the expected percentage of inhibition of the disease for the combination of the two fungicides at defined doses (for example equal to x and y respectively), x is the percentage of inhibition observed for the disease by the compound (I) at a defined dose (equal to x), y is the percentage of inhibition observed for the disease by the compound (II) at a defined dose (equal to y). When the percentage of inhibition observed for the combination is greater than E, there is a synergistic effect. Results:

TABLE 1

| Treatment 1 | Level (ppm) | Treatment 2 | Level (ppm) | Percentage efficacy | Results obtained | Percentage synergistic effect |
|---|---|---|---|---|---|---|
| Compound (Ia) | 5 | / | / | 65.7 | / | / |
| | 1 | / | / | 58.2 | / | / |
| | 0.1 | / | / | 11.9 | / | / |
| mancozeb | 25 | / | / | 17.2 | / | / |
| | 10 | / | / | 5.2 | / | / |
| | 1 | / | / | 23.1 | / | / |
| Compound (Ia) | 5 | mancozeb | 25 | 84.0 | 71.6 | +12.4 |
| | 5 | | 1 | 76.9 | 73.9 | +3 |
| | 0.1 | | 10 | 32.8 | 16.5 | +16.3 |

The compositions according to the invention comprising compound (Ia) and mancozeb as compound (II), in the (I)/(II) ratios=1/5 and 1/100, show a significant synergistic effect.

The invention claimed is:

1. A fungicidal composition comprising:
a) a pyridylmethylbenzamide derivative of formula (I):

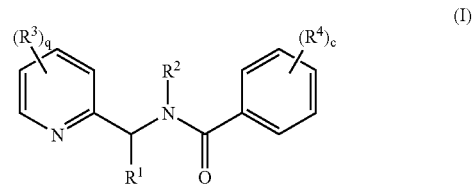

in which
- $R^1$ and $R^2$ are each hydrogen atoms;
- $R^3$ and $R^4$ are each a member selected from the group consisting of a halogen atom, a nitro radical, an alkyl radical and a trifluoromethyl radical;
- c represents 1 or 2;
- q represents 1 or 2;
- and their agriculturally acceptable optical and/or geometric isomers, tautomers and addition salts with an acid or a base;

b) a compound (II) which is a dithiocarbamate derivative having a fungicide activity selected from the group consisting of ferbam, mancopper, mancozeb, maneb, metiram, nabam, propineb and zineb, and their agriculturally acceptable isomers and addition salts with an acid; and wherein the compound of formula (I)/compound (II) weight ratio ranges from 1/500 to 30/1.

2. The composition of A claim 1, wherein
c and q are each 2.

3. The composition of claim 2, wherein the halogen atom is a chlorine atom.

4. The composition of claim 1, wherein the compound of formula (I) is a member selected from the group consisting of:
- 2,6-dichloro-N-{[3-chloro-5-(trifluoromethyl)-2-pyridinyl]methyl}benzamide;
- N-{[3-chloro-5-(trifluoromethyl)-2-pyridinyl]methyl}-2-fluoro-6-nitrobenzamide;
- N-{[3-chloro-5-(trifluoromethyl)-2-pyridinyl]methyl}-2-methyl-6-nitrobenzamide;
- and their agriculturally acceptable tautomers and addition salts with an acid or a base.

5. The composition of claim 1, wherein the compound of formula (I) is 2,6-dichloro-N-{[3-chloro-5-(trifluoromethyl)-2-pyridinyl]methyl}benzamide and compound (II) is mancozeb or propineb.

6. The composition of claim 1, wherein the compound of formula (I)/compound (II) weight ratio ranges from 1/200 to 20/1.

7. The composition of claim 1, wherein the compound of formula (I)/compound (II) ratio is between 1/100 and 1/5.

8. The composition of claim 1, further comprising at least one agriculturally suitable inert carrier and an agriculturally suitable surfactant.

9. The composition of claim 1, wherein the composition comprises between 0.00001 and 100% of the combination of the compound of formula (I) and of compound (II).

10. The composition of claim 1, wherein the compound of formula (I)/compound (II) weight ratio ranges from 1/10 to 10/1.

11. The composition of claim 1, wherein the composition is between 0.001 and 80% of the combination of the compound of formula (I) and of compound (II).

12. A method for controlling, combating, and/or protecting against phytopathogenic fungi of plants, characterized in that an agronomically effective and non-phytotoxic quantity of a fungicidal composition according to claim 1 is applied to the soil where plants grow or are capable of growing, to the leaves and/or the fruits of plants or to the seeds of plants.

13. The method of claim 12, wherein the fungicidal composition is applied by spraying a liquid to the aerial parts of the plants to be treated.

14. The method of claim 13, wherein the quantity of fungicidal composition corresponds to a dose of the compound of formula (I) and of compound (II) of between about 1 g/ha and about 10,000 g/ha.

15. The method of claim 12, wherein the quantity of fungicidal composition corresponds to a dose of compound of formula (I) and of compound (II) of between about 1 g/ha and about 10,000 g/ha.

16. The method of claim 12, wherein said plants are selected from the group consisting of grapevine, cereal crops, vegetable crops, fruit crops, sunflower, beetroot, tobacco, hop, and ornamental crops.

17. A product comprising a compound of formula (I) and a compound (II) as a combined preparation for simultaneous, separate or sequential use in controlling the phytopathogenic fungi of crops at a site, wherein said compound of formula (I) is a pyridylmethylbenzamide derivative of formula (I):

in which
- $R^1$ and $R^2$ are each hydrogen atoms;
- $R^3$ and $R^4$ are each a member selected from the group consisting of a halogen atom, a nitro radical, an alkyl radical and a trifluoromethyl radical;
- c represents 1 or 2;
- q represents 1 or 2;
- and their agriculturally acceptable optical and/or geometric isomers, tautomers and addition salts with an acid or a base;
- said compound (II) is a dithiocarbamate derivative having a fungicide activity selected from the group consisting of ferbam, mancopper, mancozeb, maneb, metiram, nabam, propineb and zineb, and their agriculturally acceptable isomers and addition salts with an acid; and
- weight ratio of said compound of formula (I) to compound (II) ranges from 1/500 to 30/1.

* * * * *

UNITED STATES PATENT AND TRADEMARK OFFICE
CERTIFICATE OF CORRECTION

PATENT NO. : 7,326,725 B2  Page 1 of 1
APPLICATION NO. : 10/493591
DATED : February 5, 2008
INVENTOR(S) : Mercer et al.

It is certified that error appears in the above-identified patent and that said Letters Patent is hereby corrected as shown below:

The title (54) and col. 1, line 1, should read:

(54) FUNGICIDAL COMPOSITION BASED ON AT LEAST ONE PYRIDYLMETHYLBENZAMIDE DERIVATIVE AND AT LEAST ONE DITHIOCARBAMATE DERIVATIVE

Signed and Sealed this

Twenty-sixth Day of August, 2008

JON W. DUDAS
*Director of the United States Patent and Trademark Office*